US008336402B2

(12) United States Patent  (10) Patent No.: US 8,336,402 B2
Glezer et al.  (45) Date of Patent: Dec. 25, 2012

(54) FLUIDICALLY-ASSISTED SENSOR SYSTEMS FOR FAST SENSING OF CHEMICAL AND BIOLOGICAL SUBSTANCES

(75) Inventors: Ari Glezer, Atlanta, GA (US); Isao Sasaki, Plano, TX (US); Jiri Janata, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 701 days.

(21) Appl. No.: 12/438,302

(22) PCT Filed: Apr. 13, 2007

(86) PCT No.: PCT/US2007/009052
§ 371 (c)(1),
(2), (4) Date: Oct. 19, 2009

(87) PCT Pub. No.: WO2008/024138
PCT Pub. Date: Feb. 28, 2008

(65) Prior Publication Data
US 2010/0229658 A1  Sep. 16, 2010

Related U.S. Application Data

(60) Provisional application No. 60/839,586, filed on Aug. 23, 2006.

(51) Int. Cl.
*G01N 1/22* (2006.01)
*G01N 1/14* (2006.01)
(52) U.S. Cl. ........... 73/863.81; 73/23.34; 73/31.02; 73/31.03; 73/64.56; 73/863.23

(58) Field of Classification Search ............. 73/23.34, 73/31.01–31.03, 31.05, 61.59–61.61, 64.56, 73/863.23, 863.31–863.33, 863.81
See application file for complete search history.

(56) References Cited

U.S. PATENT DOCUMENTS 2,555,327 A * 6/1951 Elliott ..................... 250/345
3,787,694 A   1/1974 Owen
(Continued)

FOREIGN PATENT DOCUMENTS
WO   WO 2005118138 A1 * 12/2005
OTHER PUBLICATIONS

International Search Report and Written Opinion for PCT Application No. PCT/US2007/009052 dated Oct. 1, 2007.

*Primary Examiner* — Thomas P Noland
(74) *Attorney, Agent, or Firm* — Dustin B. Weeks, Esq.; Troutman Sanders LLP

(57) ABSTRACT

The present invention is directed to devices and methods in which one or more miniature synthetic jet actuators are integrated with a chemical fluidic sensor (ChemFET) to effect inhalation and exhalation of ambient gas samples and induce small scale mixing at the surface of the sensor. The fluidically integrated jet transports ambient gas or liquid into the jet/sensor assembly through integrated gas or liquid channels, impinges the sample gas or liquid on the sensing element, and finally ejects the sample gas or liquid back into the ambient gas or liquid. The response of the sensor in the presence of the active jet is compared to its response when the jet is inactive. The jet actuator directs entrained ambient gas or liquid toward the active surface of the sensor, and the impingement of sample gas or liquid onto the surface of the sensor results in faster response time. Other embodiments are also claimed and described.

30 Claims, 10 Drawing Sheets

U.S. PATENT DOCUMENTS

| | | | |
|---|---|---|---|
| 6,082,185 A * | 7/2000 | Saaski | 73/64.56 |
| 6,083,762 A * | 7/2000 | Papen et al. | 73/863.32 X |
| 6,551,557 B1 * | 4/2003 | Rose et al. | 73/863.31 X |
| 7,105,131 B2 * | 9/2006 | Hilton | 73/863.32 X |
| 7,357,043 B2 * | 4/2008 | Cumming et al. | 73/864.33 |
| 2003/0000835 A1 | 1/2003 | Witt et al. | |
| 2003/0232425 A1 * | 12/2003 | Bachalo et al. | 435/283.1 |
| 2005/0036920 A1 * | 2/2005 | Gilbert | 422/100 |
| 2005/0054083 A1 * | 3/2005 | Vuong et al. | 435/287.2 |
| 2005/0084867 A1 * | 4/2005 | Caren et al. | 435/6 |
| 2007/0078610 A1 * | 4/2007 | Adams et al. | 702/28 |
| 2007/0144277 A1 * | 6/2007 | Padmanabhan et al. | 73/64.56 X |

\* cited by examiner

FLUIDICALLY-ASSISTED SENSOR SYSTEMS FOR FAST SENSING OF CHEMICAL AND BIOLOGICAL SUBSTANCES

BENEFIT & PRIORITY CLAIMS

This application is a 35 U.S.C. §371 US National Stage of International Application No. PCT/US2007/009052 filed 13 Apr. 2007, which claims the benefit of U.S. Ser. No. 60/839,586, filed 23 Aug. 2006. Both of said applications are hereby incorporated by reference as if fully set forth below.

GOVERNMENT LICENSE RIGHTS

This invention was made with Government support under Agreement/Contract Number NSF-EN695874, awarded by the National Science Foundation. The Government has certain rights in the invention.

TECHNICAL FIELD

The various embodiments of the present invention relate generally to the field of chemical and biological sensors. More specifically, embodiments of the present invention are directed to chemical fluidic sensors with a sniffing functionality to deliver sample gases or liquid media to the sensors and induce small-scale fluid motions near the surface of the sensors to overcome diffusion-limited mass transfer at the surface of the sensing elements.

BACKGROUND

One of the most important and technically challenging applications of fluidic sensors is in the assessment and protection of the quality of a gas, gas mixture, or liquid media ambient to a defined environment, whether such gas or other fluid is flowing or static within said environment. An example of such an application is the monitoring and protection of air typically delivered to an enclosed public place by a heating, ventilation, air conditioning (HVAC) system. Such an enclosed public place could be vulnerable to intentional or unintentional contamination by potentially harmful chemical gases or airborne biological agents introduced into the HVAC system.

The prior art contains attempts to mimic the mammalian olfaction system in the design of fluidic sensor systems. The resemblance between signal processing from multiple olfactory centers and pattern recognition technique for processing the responses of a fluidic sensor array has led to the descriptor "electronic nose," which has been successful in some applications.

The concept of an "electronic nose" generally involves the use of chemical sensors that can detect certain gas chemicals present within environmental air. Such chemical sensors operate using a chemical or biochemical reaction, in which specific reactants and catalysts must meet. In such sensors, a mass transfer step must occur to deliver reactant(s) to the surface(s) of the sensor(s) to reach catalyst(s) therein before a reaction can occur. The rate of a reaction is thus limited by the time required for diffusion of reactant(s) to the sensor surface(s).

Prior art efforts at use of an "electronic nose" in exemplary applications to monitor ambient air for potentially harmful chemical or biological contaminants has been limited by the speed at which existing sensors systems can complete the requisite reactions and provide a warning of the presence of a chemical or biological hazard. Some sensors are limited in such applications by diffusion-limited mass transfer at the surface of the sensing elements within the sensors.

BRIEF SUMMARY

Embodiments of the present invention are directed to devices and methods to provide more expedient assessment of potentially hazardous or undesired chemical or biological agents within ambient air or other gas, gas mixtures, or liquid media by integrating fluidic sensor systems with an active fluidic actuator to achieve gas or other fluid "sniffing" functionality, thereby delivering sample gases or liquid media to one or more fluidic sensors, and inducing small-scale fluid motions near the surface of the sensors to overcome the diffusion-limited mass transfer at the surfaces of the sensing elements within the sensors. Furthermore, the fluidic element can also be used to deliver a flushing gas or other fluid to clean or calibrate the sensor in long-term operation.

The fluidic functionality is achieved in embodiments according to the present invention by integrating a millimeter scale synthetic jet actuator into a fluidic sensor cell. Synthetic jets are produced by time-periodic expulsion and suction of fluid through an orifice in an otherwise sealed small cavity. The flow is induced by the motion of a diaphragm (e.g., driven by a piezoelectric element) that is integrated into one of the cavity walls. These jets are inherently zero net mass flux (i.e., composed entirely of ambient fluid) and therefore can induce directionally and spatially controlled flow field that combines sink-like entrainment of ambient fluid toward the jet orifice and source-like ejection of that fluid toward a desired target. The small-scale motions that are induced by the time periodic actuation can lead to improved transport and mixing of the entrained fluid near the sensing element. While synthetic jets can be realized over a broad range of scales, microscale jets, having orifice diameters in the range of 10-100 µm fabricated using MEMS technologies, are of particular value for integration with fluidic sensors according to the present invention In an exemplary embodiment according to the present invention, a jet actuator having a rectangular orifice generates jets normal to the surface of a fluidic sensor that is placed about eight orifice widths away. The formation of the jet induces a low-pressure domain in the vicinity of the orifice and thereby draws sample gas through an integrated conduit (that may be thought of as a "nose"). The sample gas is transported by the jet and impinges on the embedded sensor. The volume flow rate of the sample gas can be easily regulated by the amplitude of the diaphragm motion. Embodiments of the present invention thus eliminate the long transport time that is typically associated with diffusion of the sample gas toward the surface of the sensor in a conventional application. The characteristic dimensions of the jet in embodiments of the present invention are designed to scale with the active surface of the sensor for maximum coverage and sensitivity.

In an exemplary embodiment according to the present invention, the jet orifice measures 0.5×7 mm, and the amplitude of the jet velocity at the orifice is about 8 m/s (jet speeds on the order of 10-20 m/s can be easily realized, and actual jet speeds may exceed 100 m/s). The actuation frequency is about 1 kHz, and therefore, the characteristic jet period is several orders of magnitude "lower" than the response time of the fluidic sensor (1-100 s), which would normally be limited by the diffusion "through" the sensing layer.

Diaphragm pumps have been used to enhance fluidic sampling in ambient air in combination with chemical sensors. Such fluidic sampling systems were typically designed to pump sample gases to a small gas flowthrough cell where the fluidic sensor is mounted at relatively low frequencies. Unlike diaphragm pumps which use various check valves, the current jet actuator does not use any additional moving-parts hardware. In various embodiments of the present invention, the diaphragm pump and the flowthrough cell are replaced by a synthetic jet that is inherently composed of entrained ambient air and impinges directly at a desired impingement angle that can be varied between normal and tangential relative to the sensing layer of the sensor. This significantly reduces the volume flow rate of sampling gas that does not come in direct contact with the sensor and therefore reduces the overall volume flow rate. Therefore, fluidic sampling systems according to the present invention may be designed as substantially compact systems having characteristic dimensions that are commensurate with the scale of the sensors (millimeter to micrometer-scale). Furthermore, the direct impingement (and small-scale motions) of the sample gas jet on the surface of the sensor allows for additional reduction in response time when the concentration of the sample gas changes.

Embodiments of the present invention provide integrated fluidic sampling and mixing functionality by fluidic actuation that significantly improves the chemical response times of the sensor systems over existing fluidic sampling systems and techniques. Fluidic activation as employed in embodiments of the present invention may permit sampling of gases or liquid media regardless of whether the gas or other fluid is static or actively flowing. Moreover, embodiments of the present invention provide non-intrusive fluidic sampling that does not introduce other substances or otherwise change the nature of the fluid being sampled.

Still other embodiments of the present invention may combine a gas sensing array and an air purification unit, which together form a system that may be regarded as a "smart filter." Such a "smart filter" embodiment of the present invention may allow periodic differential sampling and measurement of gases "upstream" and "downstream" of a filter. In such an exemplary system, a correctly functioning filter supplies the "zero gas" from downstream to provide continuous sensor baseline correction. In a "smart filter" system according to the present invention, a synthetic jet delivers well-defined pulses of the two gases. Any deterioration of the performance of the "smart filter" may then be diagnosed from the response pattern of the sensors.

Embodiments according to the present invention may be used to monitor HVAC systems in buildings or enclosed spaces. Other embodiments of the present invention may be used as smoke and/or carbon monoxide detectors in enclosed spaces. Yet other embodiments of the present invention may be used in water treatment systems, medical applications, or in industrial applications to assay and monitor gases and/or liquids for quality control and safety purposes during the manufacture, treatment, or use of such fluids.

Other aspects and features of embodiments of the present invention will become apparent to those of ordinary skill in the art, upon reviewing the following description of specific, exemplary embodiments of the present invention in conjunction with the accompanying figures.

DETAILED DESCRIPTION OF THE INVENTION

Figure 1:
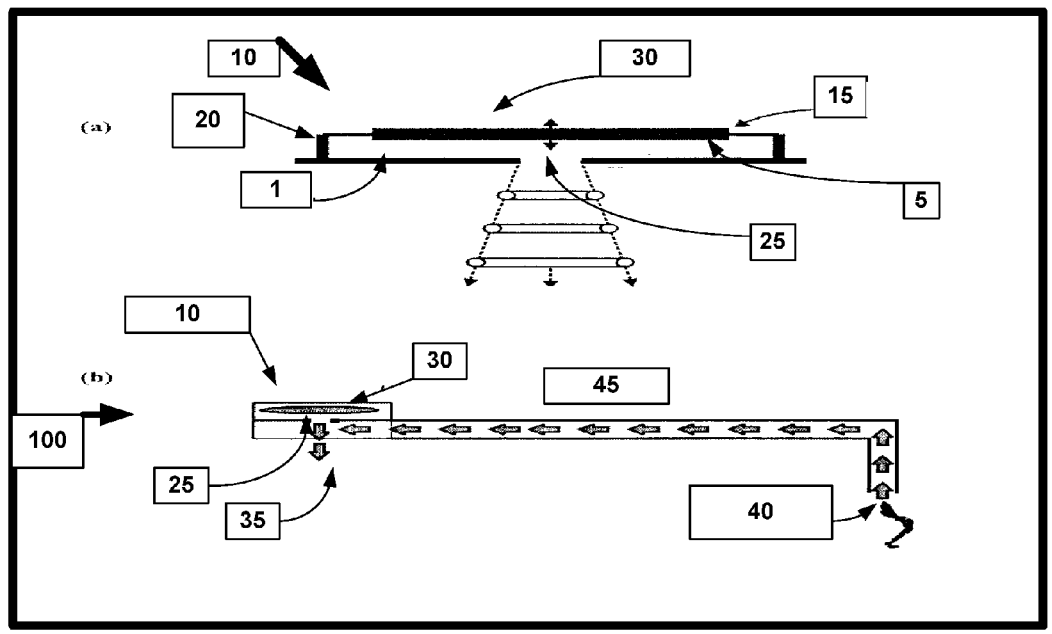
FIG. 1(a) shows a sectional view of an embodiment of a jet actuator according to the present invention.
FIG. 1(b) shows a sectional view of an embodiment of a fluidic sensing system with an integral jet actuator according to the present invention.
FIG. 1(c) shows an alternate sensor array used for gas sensing in certain embodiments of the present invention
Figure 1:
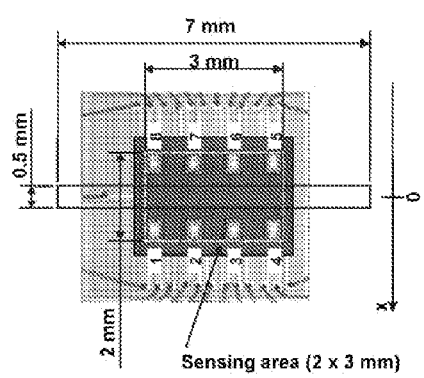

Referring now to the figures, wherein like reference numerals represent like parts throughout the several views, exemplary embodiments of the present invention will be described in detail. Throughout this description, various components may be identified having specific values or parameters, however, these items are provided as exemplary embodiments. Thus, the exemplary embodiments do not limit the various aspects and concepts of the present invention as many comparable parameters, sizes, ranges, and/or values may be implemented.

Exemplary embodiments according to the present invention comprise fluidic sampling systems with integral active fluidic actuators to deliver sample gases to the fluidic sensors and to induce small-scale fluid motion near the surface of the sensors to overcome diffusion-limited mass transfer at the surface of the sensing elements. This provides a "sniffing" functionality to the fluidic sampling systems of the present invention which is not present in the prior art. Furthermore, the fluidic elements can also be used to deliver a flushing gas or other fluid to clean or calibrate the sensors in long-term operation.

Exemplary fluidic sampling systems with integral active fluidic actuators according to the present invention may be used to assay and monitor gas or other fluid content in ambient environments, as well as in settings involving a fluid or fluid mix contained within an enclosed supply line. Furthermore, fluidic sampling systems with integral active fluidic actuators according to the present invention may be used in settings where a fluid or fluid mix is in motion, or without active flow.

According to the present invention, synthetic jets are produced by a jet actuator by time-periodic expulsion and suction of fluid through an orifice. Referring now to FIG. 1(a), a jet actuator 10 comprises a small cavity 5 is defined in a space defined by a first wall 1, a second wall 15, and sidewalls 20. The first wall 1 contains an orifice 25 but the cavity 5 is otherwise sealed. Gas or fluid flow may be induced by motion of a diaphragm 30 [e.g., driven by a piezoelectric element which is not shown in FIG. 1(a)] that may be integrated into a cavity second wall 15 as shown schematically in FIG. 1(a). Jets produced by the jet actuator 10 as shown are inherently zero net mass flux (i.e., comprised entirely of ambient fluid) and therefore can induce directionally controlled flow field that combines sink-like entrainment of ambient fluid towards the jet orifice 25 and source-like ejection of that fluid towards a desired target.

A schematic embodiment of a fluidic sensing system with an integral jet actuator according to the present invention is shown schematically in FIG. 1(b), where the fluidic sensing system 100 comprises a jet actuator 10 having an orifice 25 which impinges normal to the surface of a fluidic sensor 35 that is placed a distance away and within the flow path of a sample gas 40 within an integrated conduit 45. For example, the jet actuator orifice 25 may be located about 8 orifice widths away from the surface of a fluidic sensor 35 in one embodiment of the present invention. The formation of a jet by action of the jet actuator 10 induces a low-pressure domain in the vicinity of the orifice 25 and thereby draws sample gas through the integrated conduit 45 (that may be thought of as a "nose" with a "sniffing" action). The "sniffed" sample gas 40 is transported by the jet and impinges on the embedded sensor 35. The volume flow rate of the sample gas 40 may be regulated by the amplitude of the motion of the diaphragm 30 of the jet actuator 10.

FIG. 1(c) shows an alternate sensor array used for gas sensing in certain embodiments of the present invention with exemplary dimensions shown. The platform in FIG. 1(c) is composed of eight identical sensing modules (1-8), each of which can be used either as a chemFET or as a chemiresistor. In the center of each of the exemplary modules is the drop-cast conducting polymer, PANI•CSA, as the gate conductor. The modules are numbered 1-8 counterclockwise from bottom left. The overlaid rectangle (0.5×7 mm) indicates the orifice size of the synthetic jet actuator (not shown in FIG. 1(c)) placed above the sensing platform. The x-axis shows the direction of the offset distance between the center of the orifice and the sensing area.

The small-scale motions that are induced by the time-periodic actuation lead to improved transport and mixing of the entrained fluid near the sensing element of a fluidic sensor which is typically diffusion-limited. While synthetic jets can be realized over a broad range of scales, micro-scale jets (having orifice diameter in the range of 10-100 µm) that are fabricated using MEMS technologies are of particular interest for integration with fluidic sensors.

Fluidic sampling systems according to the present invention eliminate the long transport time that is associated with diffusion of the sample gas towards the surface of a sensor in existing fluidic sampling systems. The characteristic dimensions of the jet in embodiments of the present invention may be designed to scale with the active surface of the sensor for maximum coverage and sensitivity. In some exemplary embodiments of the present invention, a jet orifice that is generally rectangular and measures about 0.5 mm×7 mm and the amplitude of the jet velocity at the orifice is about 8 m/sec, resulting in exemplary jet speeds on the order of 10-20 m/sec. In such embodiments of the present invention, the resulting actuation frequency is about 1 kHz and therefore the characteristic jet period is several orders of magnitude lower than the response time of the fluidic sensor (1 to 100 sec), which is normally limited by the diffusion through the surface of the sensor. Other embodiments of the present invention may employ other sized- and shaped-orifices and/or differing jet velocities.

It is notable that, in embodiments according to the present invention, the nature of the interaction of the jet and the surface of the sensor is dynamic, with the pulsatile jet(s) inducing pulsatile, unsteady motion at the sensor surface.

The desired power used for the jet generation in various embodiments of the present invention may be as low as possible to reduce the sound noise from the diaphragm and the power consumption by the jet actuators. If the power consumption of the jet actuator is a concern, the jet actuator may be operated in an interrupted manner (using programmable operation) to save the power consumption.

Fluidic sensors in some exemplary embodiments of the present invention may be constructed using a ChemFET (Chemically sensitive Field Effect Transistor) device with a drop-cast conducting polymer film as gate conductor. Some ChemFET devices used in embodiments of the present invention are further described in "Chemical Modulation of Work Function as a Transduction Mechanism for Chemical Sensors," J. Janata and M. Josowicz, *Acc. Chem. Res.* 1998, vol. 31, pp. 241-248.

Figure 2:
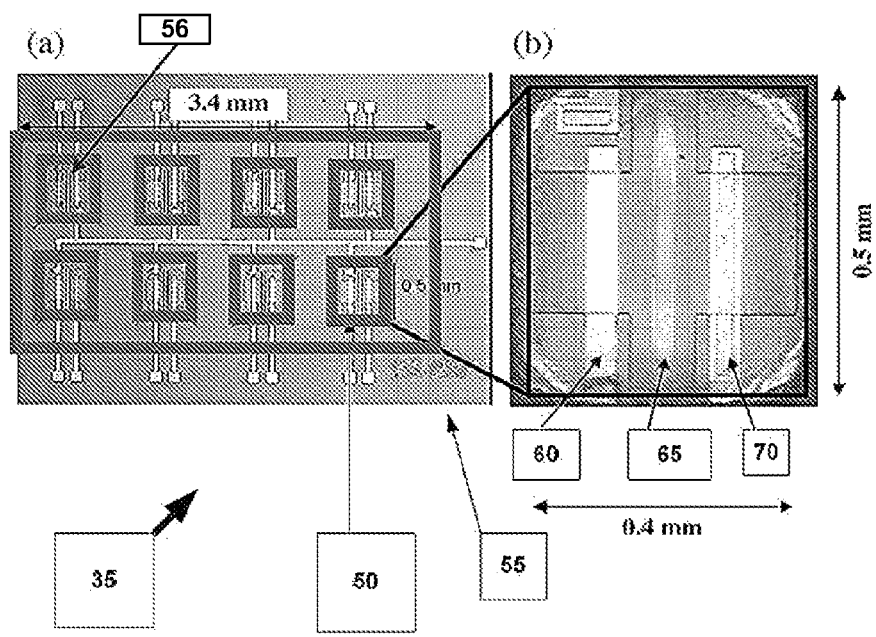
FIG. 2(a) shows an overview of an exemplary fluidic sensor of the present invention with an eight element die containing eight chemFET devices.
FIG. 2(b) shows a detail of a chemFET device of the present invention.

In such embodiments, the die may have one or more individual ChemFET devices on the same surface. In FIG. 2(a), an exemplary embodiment of a fluidic sensor 35 of the present invention is shown with eight individual ChemFET devices 50 on the same surface of a die 55, in which each ChemFET device 50 is separated by micro-structured wells 56 to allow casting different films on the same die 55. An individual ChemFET device 50 is shown in detail in FIG. 2(b), comprising a drain 60, a gate 65, and a source 70.

Embodiments of the present invention may employ one or more sensors, each of which may contain one or more individual ChemFET devices. Any desired level of scaling is therefore attainable using various configurations of fluidic sampling systems with integral active fluidic actuators according to the present invention. In embodiments of the present invention in which sensors are clustered, redundancy may provide a fail-safe mechanism to reduce aberrant sensor readings.

In some exemplary fluidic sensors of the present invention, polyaniline (PANI) doped with camphorsulfonic acid (CSA) is used as the sensing material. Following a cleaning procedure of undoped PANI powder (polyaniline emraldine base), 50 mg of the dry PANI powder (Aldrich) is dissolved in 10 mL of 88% formic acid (Fisher Scientific) with ten minutes of sonication followed by overnight stifling. Then, (1R)-(–)-10-camphorsulfonic acid (Aldrich) is dissolved into the solution with ten (10) minute sonication to dope PANI (polyaniline salt) so that there are two CSA molecules per four benzene units of PANI ($PANI(CSA)_{0.5}$). This stock solution is further diluted (5 times) with formic acid and films are drop-cast onto each ChemFET device using a glass capillary (the volume of the solution dispensed is ca. $0.02\ mm^3$). The films are dried at 60° C. for 24 hours. FIG. 2(b) shows an image of a ChemFET device with a dropcast $PANI(CSA)_{0.5}$ film. The gas sensing response of a ChemFET device is measured as a change in the gate voltage with a constant drain-source current of 0.2 mA.

Figure 3:
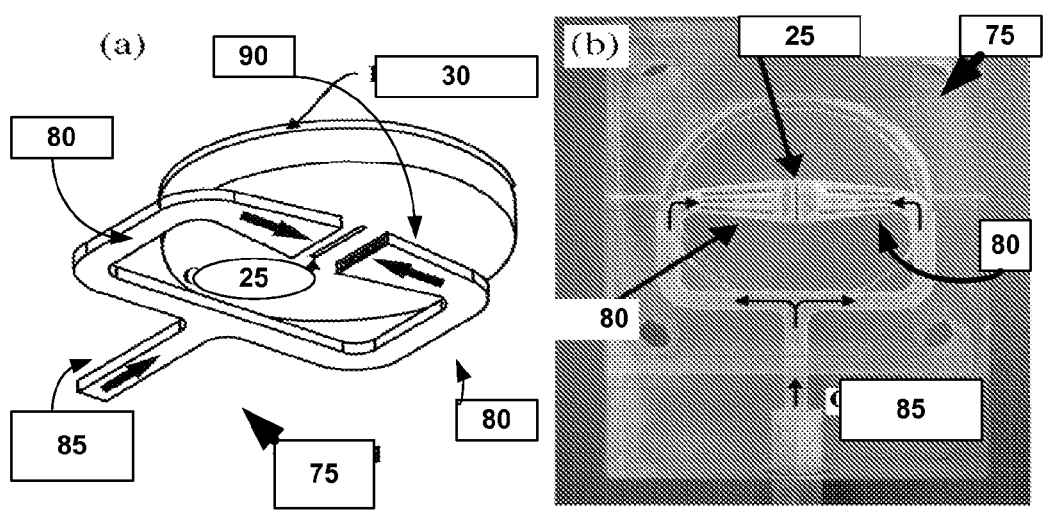
FIG. 3(a) shows a schematic diagram of a jet actuator module according to the present invention.
FIG. 3(b) shows a schematic diagram of a fabricated fluidic module according to the present invention.

Jet actuators with fluidic manifolds integrated with synthetic jet modules in some exemplary embodiments of the present invention may be fabricated using stereolithography. The manifold 75 which is shown schematically in FIG. 3(a) has two branches 80 that are connected to a single feed line through an inlet 85. In an exemplary embodiment of the present invention as shown in FIG. 3(a), each branch 80 terminates in a rectangular duct 90 along each of the long sides of a similarly rectangular jet orifice 25. Other shapes and dimensions may be used in other embodiments of the present invention. When the exemplary jet is active, sample gas is drawn through the inlet 85 of the manifold 75 and pulsatile flow through the orifice 25 directs the gas normal to the surface of a sensor (not shown in FIG. 3(a)).

An image of the fabricated fluidic module before the assembly of the driver diaphragm is shown in FIG. 3(b). In one embodiment of the present invention, the fluidic manifold 75 is connected to an inlet tube 85, which may have an internal diameter of 3.9 mm. In this exemplary embodiment, the diaphragm (not shown in FIG. 3(b)) may be a unimorph construction of a 30.5 mm diameter thin metal disk that is bonded to a piezoceramic element (smaller diaphragms and/or diaphragms of other materials can be implemented in other embodiments of the present invention). In the exemplary embodiment of the present invention as shown in FIG. 3(a), each branch 80 terminates in a rectangular (1.5×7 mm) duct 90 along each of the long sides of a similarly rectangular jet orifice 25 (0.5×7 mm). In the particular example shown in FIG. 3(b), the depth of the jet cavity is 1 mm and the diaphragm is driven at its resonance frequency (ca. 1 kHz at up to 37 $V_{rms}$). Furthermore, in the particular example shown in FIG. 3(b), the distance between the orifice 25 and the sensor (not shown in FIG. 3(b)) is 4 mm and the jet is designed so that it impinges on all eight ChemFET devices of the sensor.

In one exemplary embodiment of the present invention, only one ChemFET device is used to compare the chemical response times in the presence and absence of the jet. In other embodiments of the present invention, comparisons may be made between the characteristic response times of the sensor when the jet is inactive and the sample gas (such as ammonia) is transported by diffusion only, and when the sample gas is transported and mixed by the jet actuator. As noted previously, two separate gas sources may be used. In such an example, the first source is the vapor that forms above a 29.3% ammonium hydroxide solution (Fisher Scientific) which may be thought of as a sample of the gas that is released from a spilled volatile solution. The second source is a pressurized reservoir of 5.14% ammonia gas (Matheson) that is released to the atmosphere and may be thought of as a sample from a continuous leak of a pressurized container.

Example 1

Figure 4:
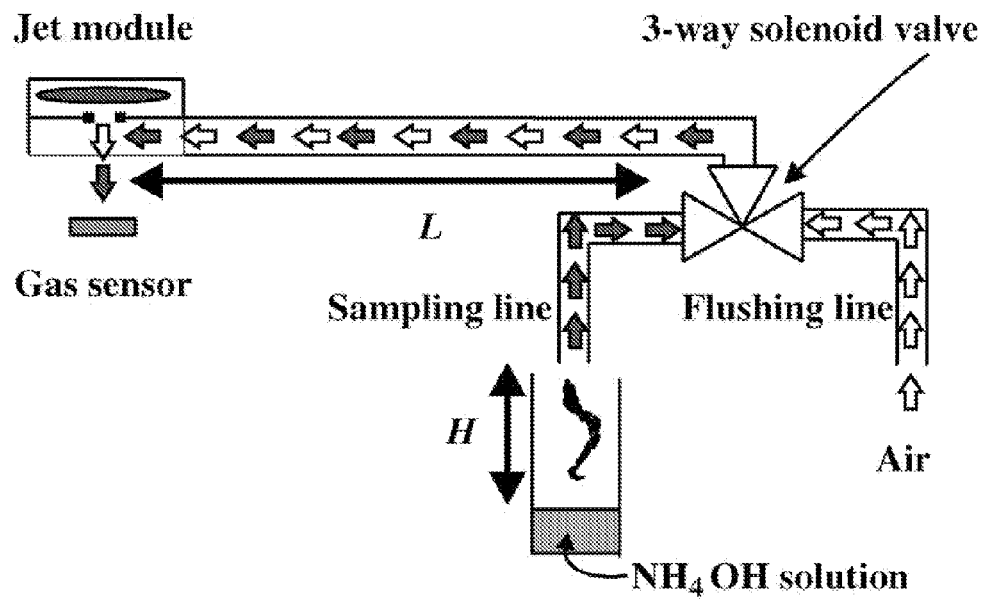
FIG. 4 shows an exemplary setup of the present invention for fluidic sampling with two different gas sources.
Figure 4:
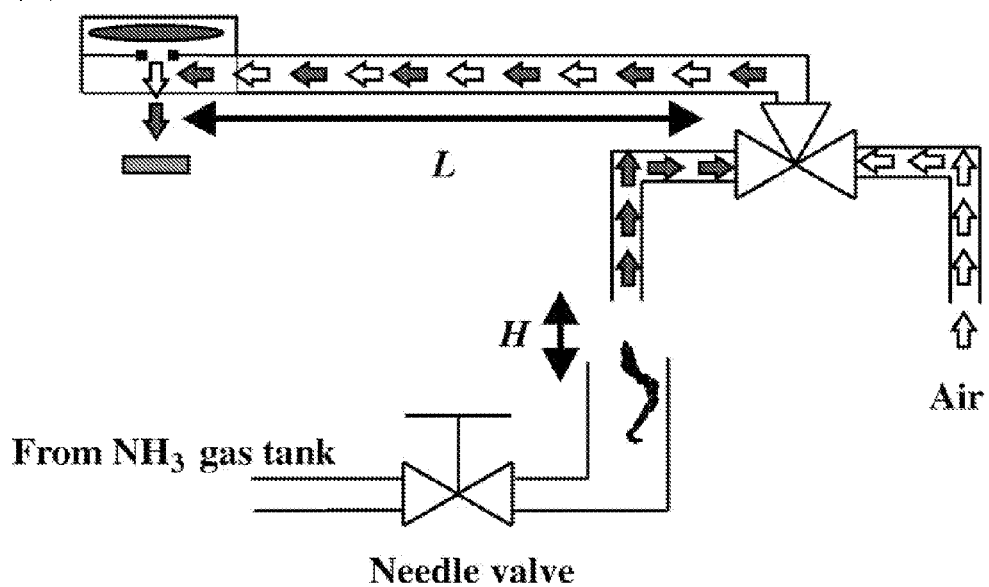
Figure 5:
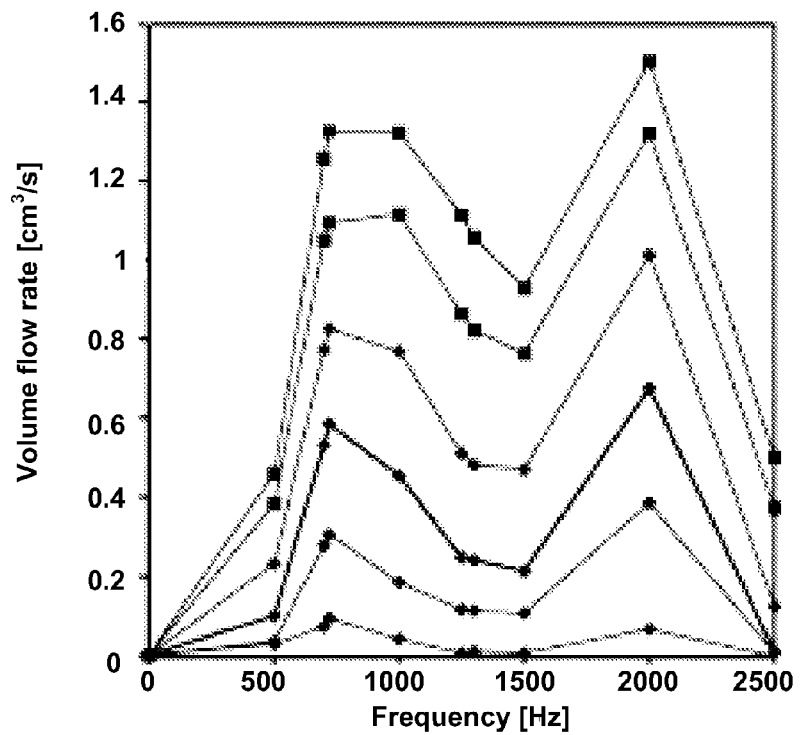
FIG. 5 is a graph showing the variation of the flow rate computed from pressure drop measurements with frequency and actuator voltage in an exemplary embodiment of the present invention.

An exemplary setup of the present invention for fluidic sampling with two different gas sources [(a) vapor above ammonium hydroxide solution and (b) leakage of ammonia gas through a needle valve] is shown schematically in FIG. 4. A three-way solenoid valve (ASCO) is used to switch between the sample gas line and cleaning (flushing) gas that is simply the ambient air which is pumped and transported to the sensor by the jet actuator. The induced flow rate over a range of supplied voltages for jet flows is computed from pressure drop measurements based on laminar Poisseuile flow in the feed tube (L=128.5 cm) using a micromanometer (Dwyer) that can resolve 0.00635 mm-$H_2O$. The variation of the flow rate (computed from pressure drop in the tube) with actuation frequency (F) is shown in FIG. 5 for different actuation voltages ($V_{AC}$). The data in FIG. 5 show two distinct peaks at the diaphragm's fundamental (nominally 1000 Hz) and second-harmonic resonances. While the flow rate evidently increases with actuation voltage, the increase is non-linear and appears to saturate as the voltage increases (e.g., at 2000 Hz, the flow rate increases from 1.3 to 1.5 $cm^3$/s as the actuation voltage increases from 26 to 37 $V_{rms}$) indicating that for a given diaphragm the power dissipated increases nonlinearly with volume flow rate. The calculated nominal velocity magnitude at the exit plane of the jet in this example is 8 m/s at F=720 and 1000 Hz ($V_{AC}$=37 V) where the corresponding volume ejected per stroke is 0.483 $mm^3$ and the jet Reynolds number is 3100, based on the centerline velocity.

Figure 6:
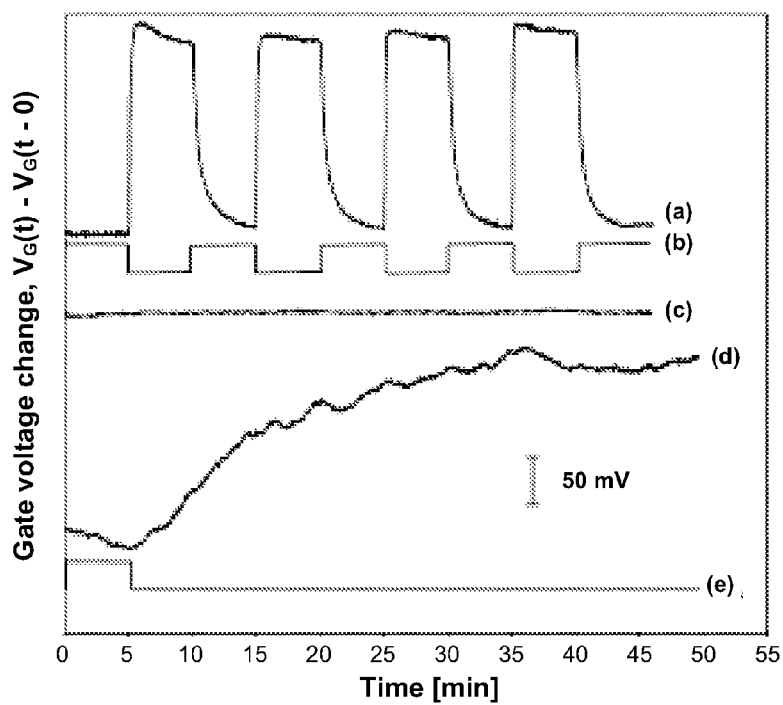
FIG. 6 is a graph showing the response of the sensor to the induced flow of ammonia gas formed above ammonium hydroxide solution as the three-way valve is switched between the ammonia and flushing air lines at five-minute intervals in an exemplary embodiment of the present invention.

A exemplary sample of the responses of ChemFET sensors of the present invention to the induced transport of vapor from the ammonium hydroxide solution when the intake port is aligned coaxially with the vial is shown in FIG. 6, curve (a), where (F=1500 Hz, $V_{AC}$=37 V, H=2 cm and L=17 cm. The corresponding switching time trace of three-way solenoid valve between the ammonium vapor source and pure air at 5-min intervals is shown in FIG. 6, curve (b), in which it should be noted that when the valve signal is low it is switched to the $NH_3$ line in this example. The time trace for the control experiment in the absence of the $NH_4OH$ solution (i.e., both lines are flushing with air) is shown in FIG. 6, curve(c), which confirms that there are no changes in the sensor output due to the switching of the solenoid valve or residual gases in the exemplary system. The response of the sensor in the absence of the jet is shown in FIG. 6, curve(d) when the vapor is delivered by "natural" diffusion through the tube. In such an exemplary control demonstration of the present invention, the three-way vale was kept open to the ammonia line after a five minute flushing interval with pure air, as shown in FIG. 6, curve(e). These data according to exemplary embodiments of the present invention show that in the presence of the jet, the response time of the sensor is remarkably faster by about two orders of magnitude (20 compared to 1800 seconds) showing that fluidic actuation significantly improves the detection performance by adding "sniffing" and mixing functionality.

In exemplary embodiments of the present invention, a minimum actuation voltage ($V_{AC}$) may be defined, where $V_{AC}$ is the minimum power required to pump gases without degrading the response time. In embodiments of the present invention, while the flow rate increases with $V_{AC}$, the increase is nonlinear and appears to saturate as the voltage increases (e.g., at 2000 Hz, the flow rate increases from 1.3 to 1.5 cm$^3$/s as the actuation voltage increases from 26 to 37 $V_{rms}$), indicating that for a given diaphragm, the "dissipated" power increases nonlinearly with $V_{AC}$. Meanwhile, when the power is higher than 100 mW, the normalized 90% response times for all tube lengths are constant (ca. 20 s) and comparable to the time required for the NH$_3$ gas to diffuse through the film when the film thickness and apparent diffusion coefficient are assumed to be 200 nm and 5×10$^{-11}$ cm$^2$/s, respectively. Thus, when the 90% response time is ca. 20 s, the limiting step of the response is the diffusion of the gas through the film. Further, when $V_{AC}$ is higher than 20 V, the 90% response times for all the distances are approximately the same (ca. 20 s).

When the vapor above the ammonium hydroxide solution was used as the gas source and the exposure time was extended longer than five minutes, the response started to decrease and reached a lower plateau (data not shown). This effect is because the volume of the headspace vapor is finite, and the sample gas flux becomes limited by the vaporization of the solution. This decrease of the signal is observed during the first exposure to "wet" NH$_3$ in FIG. 6a, which is not the sensor drift. In order to eliminate this effect in the presently disclosed example of the present invention, an ammonia gas tank with a needle valve as a continuous gas source was employed. In this example, the sensor responses kept a steady value even with extended exposure times (FIGS. 7(a) and 8(a)). Nevertheless, both types of gas sources are valid for testing real applications of the present invention. FIG. 6 shows that the sensor response time became much faster when the jet was on (FIG. 6, curve (a)) compared with the one when the jet was off (FIG. 6, curve (d)) (the gas was delivered only by diffusion). This result suggests that for critical applications of a fluidic sensor system, an addition of the jet pumping system according to the present invention is effective in improving the response time of a sensor system. As shown in FIG. 4(a), the jet cell with a three-way (or multi-way) valve upstream enables a user to introduce two gas lines (or more) into a single sensing device in various embodiments according to the present invention.

In a similar demonstration, an exemplary embodiment of the present invention was used to assess the sensor response to ammonia gas release (leakage) from a pressurized (40 psi) NH$_3$ tank (FIG. 4(b)). In this case, the released leakage jet was directed towards the system tube to allow forced convection of the ammonia towards the sensor even in the absence of jet actuation. The response of the sensor is shown in FIG. 7(a) (here L=17 cm, F=1000 Hz, $V_{AC}$=37 V and H=0.5 cm). The solenoid valve was controlled in the same manner as in FIG. 6(b) (when the valve signal is low, the sensor was switched to the NH$_3$ line).

Figure 7:
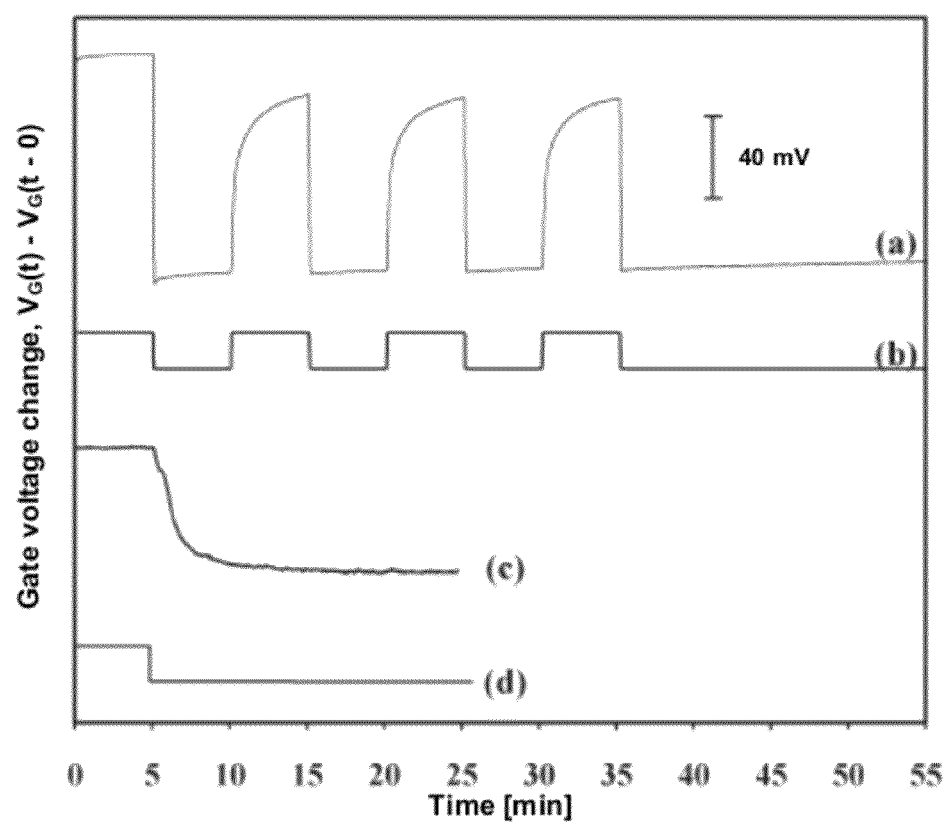
FIG. 7 is a graph showing sensor response to an ammonia gas jet released from pressurized tank through a needle valve as the three-way valve is switched between the ammonia and flushing air lines at five minute intervals in an exemplary embodiment of the present invention.
Figure 8:
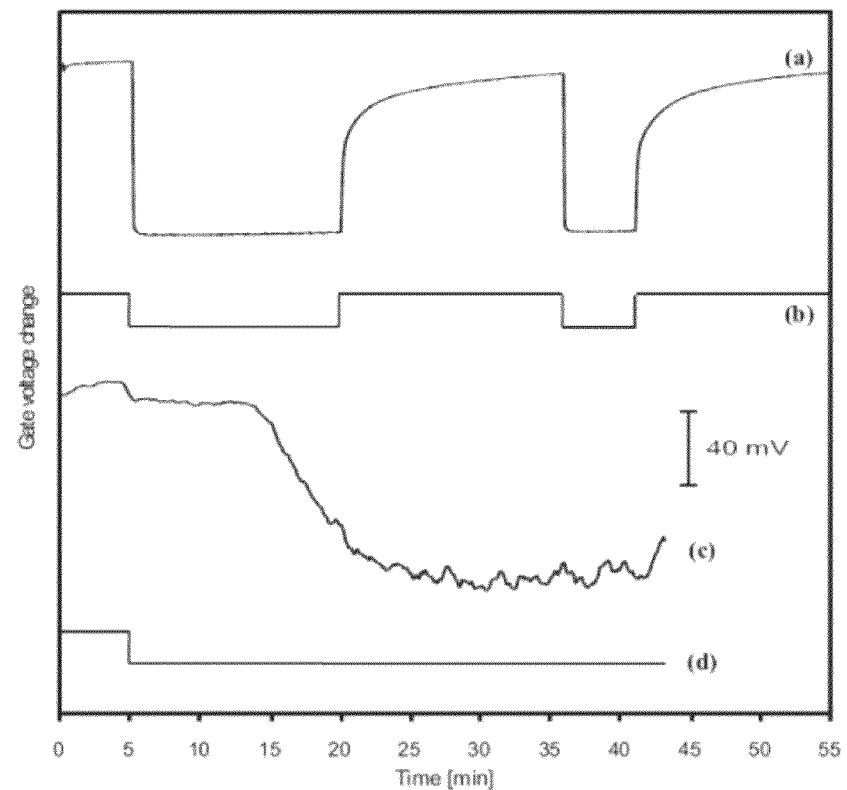
FIG. 8 is a graph showing sensor response to an ammonia gas jet released from pressurized tank through a needle valve as the three-way valve is switched between the ammonia and flushing air lines at five minute intervals in an exemplary embodiment of the present invention with longer tube length than in FIG. 7.

Despite the fact that the response in the absence of the actuator jet was assisted by the leak jet, the actuator jet still improved the sensitivity of the system by more than an order of magnitude. While the response in the presence of the actuator jet is about 20 seconds, this response degraded to 600 seconds when the jet is turned off. The exemplary data shown in FIG. 7 are repeated for a longer feed tube (L=120 cm) and the response is shown in FIG. 8(a). Despite the fact that the leak jet was inducing convection in the feed tube, the sensor's response in the absence and presence of the actuator jet decreased from 1800 to 20 seconds. This indicates that as the length of the feed tube increases (or alternately the distance from the source), the effect of the jet actuator become more pronounced in overcoming diffusion-limited transport.

Figure 9:
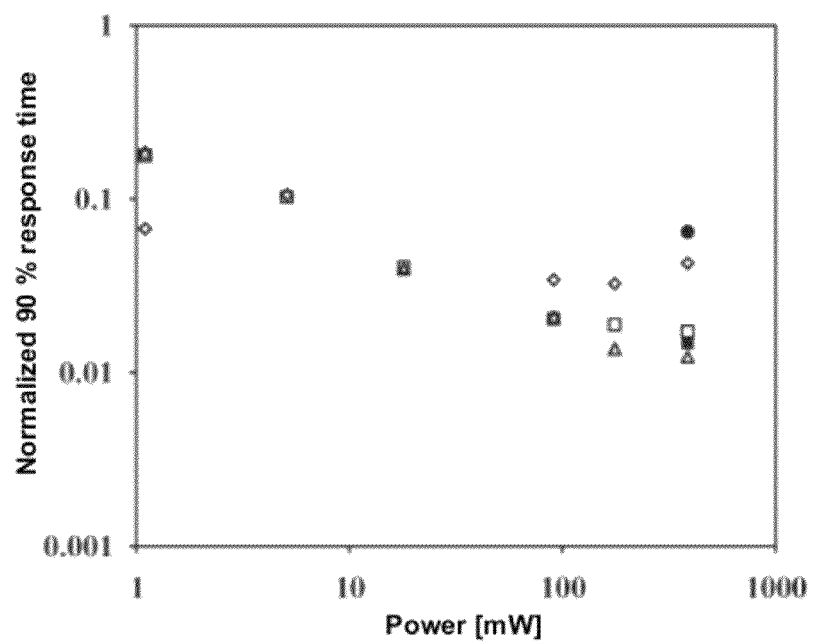
FIG. 9 is a graph showing variation with actuation power of the characteristic normalized sensor response time (based on 90% of steady state when the jet power is zero) to gaseous ammonia for three different feed tube lengths.

Data for the performance of the jet actuator for a range of feed tube lengths (from 17 to 120 cm) and actuation power is shown in FIG. 9. The characteristic time required to reach 90% of the steady sensor output (following the switching transient) is measured for ammonia gas released from the pressurized NH$_3$ tank (FIG. 4(b)). These data show that while at low actuation power the effectiveness of the jet diminishes, there is typically no advantage in increasing the actuation power beyond a certain level because the response of the sensor is limited by internal diffusion (the apparent diffusion coefficient for a film thickness of 200 nm is 5×10$^{-11}$ cm2/s). In fact FIG. 9 shows that when the power is higher than 200 mW, the 90% response time is almost independent of the length of the feed tube (about 20 seconds). These data also indicate that significant performance improvements can be achieved even at low actuation power (clearly, no attempt was made here to optimize the performance of the actuator's diaphragm). When acoustic emission is an issue, the jet can be efficiently driven using electromagnetic diaphragm that operates at frequencies on the order of 100 Hz. The present data suggests that even at these frequencies the actuation period is still far lower than the characteristic response time of the actuator itself and therefore no significant performance degradation is anticipated. Another way to conserve actuation energy is to operate the actuator in a time-modulated sequence since it can be easily turned on and off.

Embodiments of fluidic sensor systems with integral jet actuators of the present invention can be applied to many situations. It is, for instance, possible to use embodiments of the present invention to examine and compare several gases by switching between the lines (differential sensing) to check before and after a process (e.g. filtering, cleaning, or catalytic converting), and to give an alarm when the process ceases to work properly (e.g. a filter change alarm). It is also possible to use embodiments of the present invention to connect one of the gas lines to a background (carrier) gas, or a known concentration gas source (reservoir delivery) to refresh or recalibrate the fluidic sensors. These gases can be stored in a small pressurized gas cartridge due to the small volume of the gas required for the sensors. Embodiments of fluidic sensor systems with integral jet actuators of the present invention thus solve the notorious baseline drift of existing fluidic sensors.

Example 2

In the following example of an embodiment of the present invention, a fluidic sensor array was integrated into a sensing platform containing eight identical sensing modules separated by micro-structured wells into which a chemically sensitive layer was cast. Each of the modules may be operated in the chemFET (chemically sensitive Field Effect Transistor) or chemiresistor mode. When the sensing platform was operated in the chemFET mode, the change in the gate voltage was monitored at an applied constant drain-source current of about 0.2 mA in the source-follower configuration. FIG. 1(c) shows the exemplary modules with drop-cast films of polyaniline (PANT) doped with (1R)-(−)-10-camphorsulfonic acid (CSA, Aldrich). The stock solution was prepared by dissolving 50 mg of the purified PANI emeraldine base powder (MW 20 000, Aldrich) in 10 mL of formic acid (88%, Fisher Scientific), followed by sonication for 10 minutes and overnight stirring in a closed container. The PANI/CSA solution was prepared by adding 6.4 mg of CSA per 1 mL of the PANI stock solution. The amount of CSA added to the PANI stock solution was such that there are two CSA molecules per four phenylene rings of the PANI. The obtained PANI/CSA solution was further diluted with equal volumes of formic acid.

After casting PANI/CSA films using a glass capillary, the films were dried at 60° C. overnight and then illuminated with a UV lamp at 254 nm for 90 minutes to improve the long-term stability of the sensors. The basic characteristics of the eight individual modules were examined with a semiconductor parameter analyzer (HP 4155A). The threshold voltages ($V_T$) in the chemFET mode were determined by measuring the drain-source current and scanning the gate voltage, $V_G$, from about −1 to 5 V while keeping the drain voltage, $V_D$, constant at 5 V. The resistance of the sensing film was determined by operating the sensing platform in the chemiresistor mode and measuring the current between the two gate contacts while scanning the voltage from 0 to 1 V. The averages and standard deviations of the measured $V_T$ values of chemFETs and the film resistances of chemiresistors were 844±29 MV and 5.42±1.22 MΩ, respectively. The standard deviation of the $V_T$ values with respect to the average value is smaller than that of the film resistances. This is because the polymer solution was dispensed onto each module with a capillary glass, which is not an accurate way to deliver a controlled volume of the solution and to obtain uniform film thicknesses. The film resistance depends on the film thickness, whereas the $V_T$ depends on the charge at the interface between the gate conducting layer and the insulator. Therefore, the standard deviation of the film resistances was larger than the standard deviation of the $V_T$ values.

In this example, in order to use the diagnostic power of the differential mode of measurement, sharp, rectangular pulses of gas were delivered to the sensor modules. The detailed design of the synthetic jet has already been reported. The rectangular orifice and sensing platform were oriented so that the long sides of both the orifice (0.5×7 mm, represented by the rectangle in FIG. 1(c) and the sensing area (2×3 mm) were parallel to each other, as indicated in FIG. 1(c). The streamwise distance between the orifice (the exit of the jet) and the surface of the sensing platform was chosen to be 4 mm, based on the Schlieren jet from a similar sized orifice (0.5×7.5 mm). At a streamwise distance of 4 mm, the jet spread from the size of the short side of the orifice (0.5 mm) to ca. 3 mm, which is larger than the short side of the sensing area (2 mm). The sensors were calibrated before use with an Environics 4000S (Environics, Inc.) dilution system. The sensors were placed in a stainless steel gas flow-through cell connected to the Environics system. The gas flow rate through the cell and the internal dead volume of the cell were 100 cm³ s⁻¹ and ca. 1.2 cm³, respectively. The ammonia concentrations were varied by changing the flow rates of the mass flow controllers connected to the air (Airgas) and ammonia (5.14%, Matheson) gas tanks. The flow was programmed with the Environics Series 4000 software to deliver ammonia concentration steps from 0 to 64, 257, 612, 2142 ppm and back down to 0 ppm.

Figure 10:
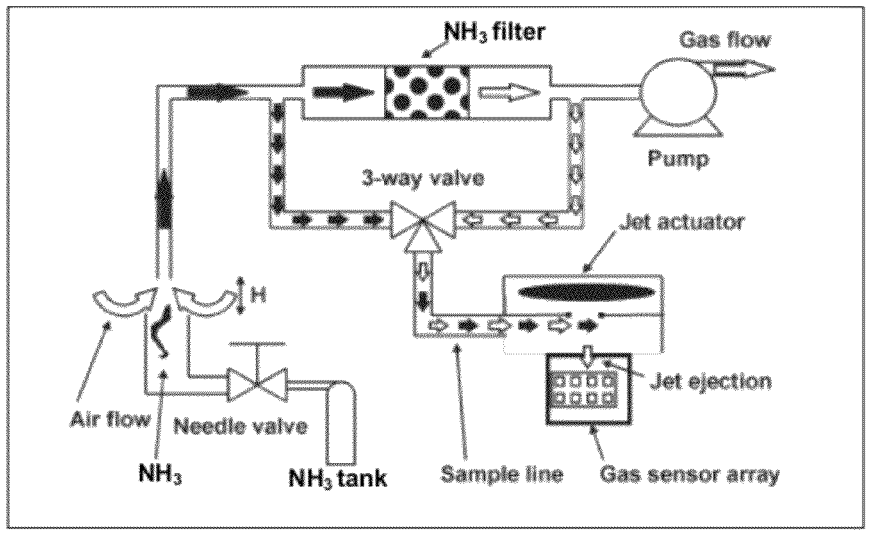
FIG. 10 shows a schematic setup for testing filter performance in an exemplary embodiment of the present invention.

In this example, a filter was incorporated as shown in FIG. 10. The main flow (indicated by the large arrows) passing through the filter zeolite was driven by a pump. The zeolite (5 Å, Fisher Science) was used after heating in an oven at 150° C. for one hour, placed in a 2.5 cm. (inner diameter) glass tube, sandwiched by porous supports on both sides, and allowed to cool at room temperature for 1 hour with the main flow driven by the pump. The amount of zeolite was changed (2 g, 4 g, and 6 g) to observe the onset times of the breakthrough of the filter (filter lifetimes). The ammonia gas released from the gas tank (5.14%, Matheson) through a needle valve was introduced into the main flow with the ambient air by the pump. The dark arrows in FIG. 10 indicate the gas contains ammonia, whereas the white arrows in FIG. 10 indicate the gas is clean after the filter. The large and small arrows represent the gas flows driven by the pump and the jet actuator, respectively. The distance between the main flow inlet port and the ammonia gas exit (H) was kept at about 1 mm so that the incoming ammonia concentration was kept constant. The normal laboratory air was used as a carrier gas. The main flow was set more than ten times higher (460 cm³ s⁻¹ when without zeolite) than the one from the jet sampling (35 cm³ s⁻¹ when the power supply to the diaphragm and the frequency were set at 91 mW and at 720 Hz, respectively) so that the jet sampling did not influence the main flow direction.

To monitor the difference of the ammonia concentrations before and after the filter (differential sensing), a three-way valve (ASCO) was switched between the two lines at switching intervals of five minutes. The onset of the breakthrough of the filter was monitored by comparing the sensors' responses measured before (upstream) and after (downstream) the filter.

Figure 11:
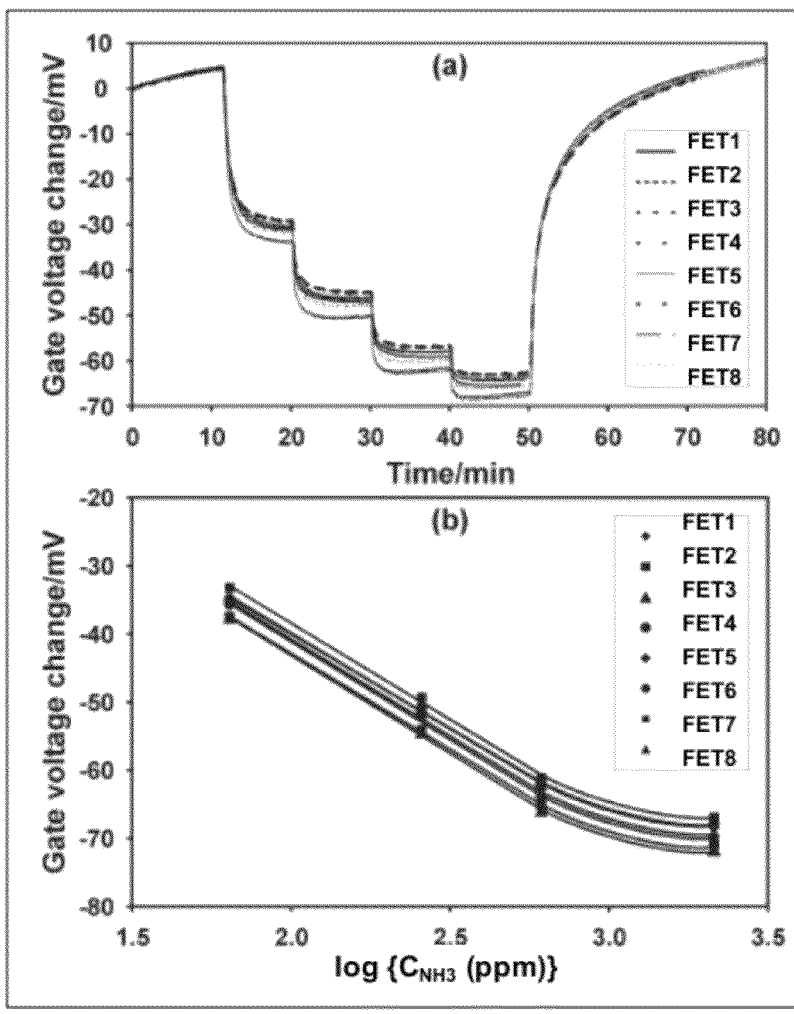
FIG. 11 is a graph showing responses of the array of the eight chemFET sensors modified with PANI•CSA film to ammonia gas in an exemplary embodiment of the present invention.

Responses of the chemFET sensor array to ammonia gas were calibrated with the conventional, pressure-driven gas delivery system using the Environics system and the results are shown in FIG. 11. It may be seen in FIG. 11(a) that all eight chemFETs show similar responses to the same concentrations of the $NH_3$ gas. FIG. 11(h) shows that changes of the measured gate voltage as a function of the logarithm of ammonia concentration have a linear dependence. The data point for the highest concentration (2142 ppm) deviates from the linear approximation indicating the saturation of the sensor signal. The calculated sensitivity of the eight chemFETs within the linear dynamic range was −28.3 mV per decade of concentration.

Figure 12:
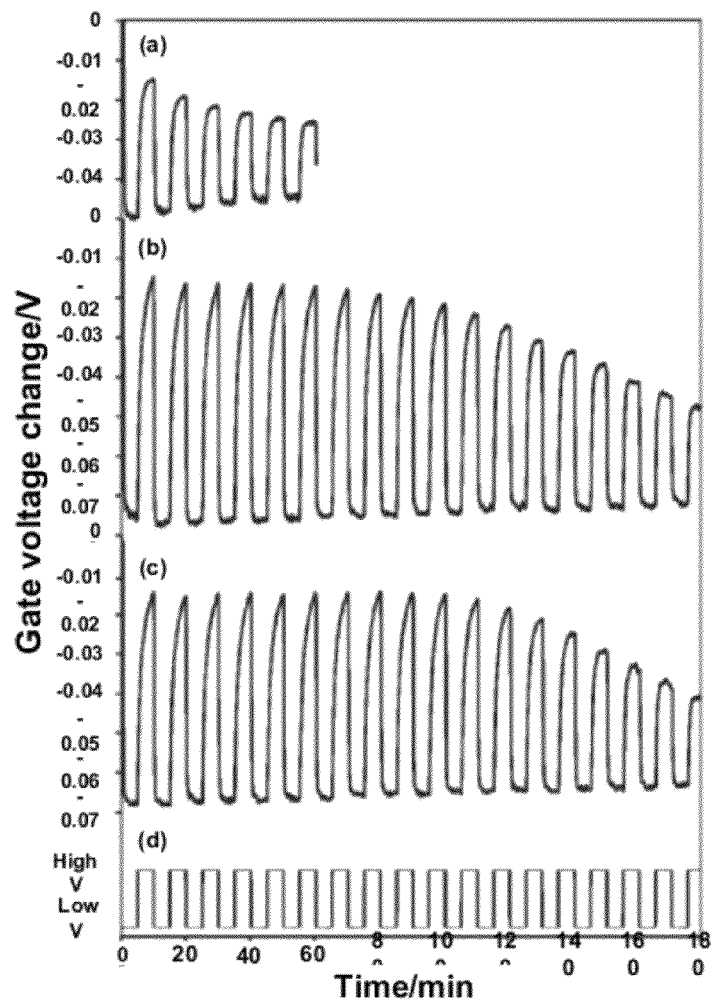
FIG. 12 is a graph showing a test of capacity of the filter in an exemplary embodiment of the present invention with the responses of a single representative chemFET to the gas before (upstream) and after (downstream) ammonia filtering using different amounts of zeolite.

Responses of one chemFET representative of the array are shown in FIG. 12. By using different amounts of zeolite [FIG. 12(a) 2 g, (b) 4 g, and (c) 6 g], the filter capacity was varied. The timing trace of the voltage signal (V) to control the three-way valve is shown in FIG. 12(d) (when V is low, the upstream is sampled and when V is high, the downstream is sampled). The tests were initiated at t=0 and the introduction of the ammonia gas into the main flow began at t=0.3 min. All the measurements were started with the three-way valve switched to the gas line before the filter (upstream). When the three-way valve was switched to the upstream gas, the gate voltage change should show a stable value if the incoming ammonia gas concentration is constant. The gradual upward shift of the gate voltage change measured with time, appearing prominently in FIG. 12(a), suggests that the incoming $NH_3$ concentration is changing or the sensor is losing its sensitivity, as explained below. On the other hand, the decrease of the gate voltage change after the filter (downstream when "High V") indicates the onset of the breakthrough of the filter, and eventually the difference between the upstream and the downstream becomes zero as the filter begins not to function at all. For example, the onset of the breakthrough of the filter in FIG. 12(c) starts after ca. 110 minutes. In this example, the synthetic jet delivered the gas in a stable and geometrically well-defined pattern to the sensing array. The exemplary sampling system was designed such that the sampled, impinging jets covered all the eight sensing modules especially when eight different sensing layers with different selectivity were formed on the sensing platform.

Figure 13:
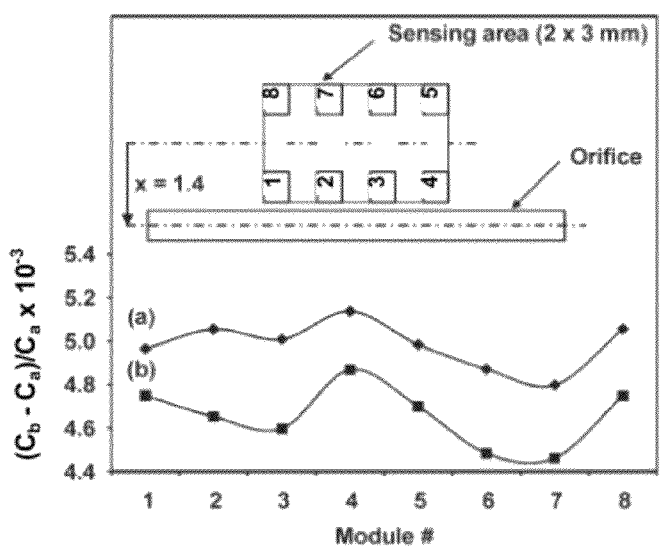
FIG. 13 is a graph showing normalized changes of ammonia concentration calculated from the response equation for the modules (1 to 8) as a function of the offset (distance x between the center of the orifice and the center of the sensing area) in an exemplary embodiment of the present invention.
Figure 14:
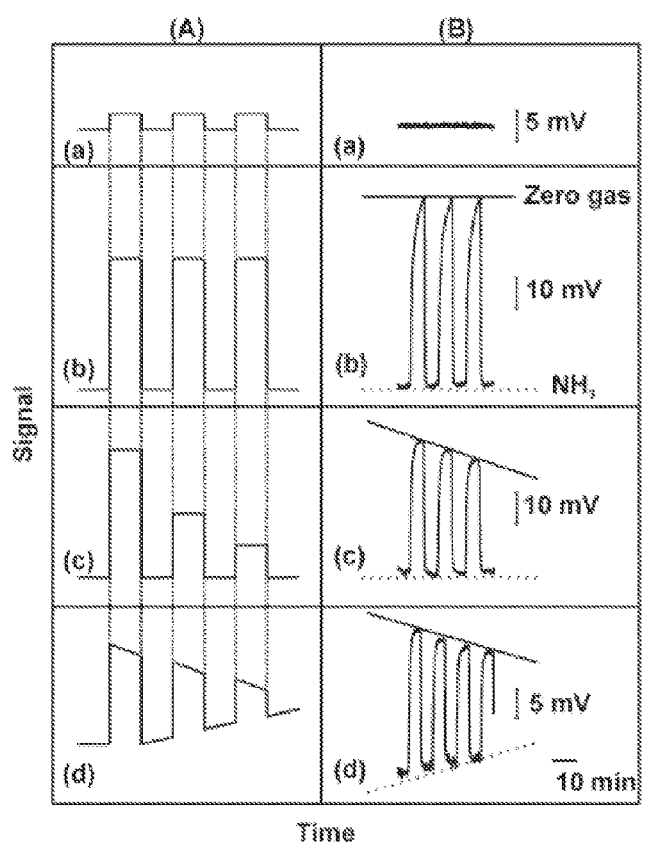
FIG. 14 is a graph showing predicted (column A) and experimental (column B) sensor signal responses from the sensor-filter combination) in an exemplary embodiment of the present invention.

Although other embodiments of the present invention may have an array for multiple gases, in this example the response was examined for only one type of selective ChemFET to ammonia gas. Using the sensors in the array that have the same sensitivity (FIG. 11) allowed the assessment of the effect of the geometry of the designed synthetic jets on the sensitivity of the individual modules in the array. To investigate the two-dimensional concentration distribution of the ammonia gas over the sensing platform, the horizontal offset of the jet was displaced by x=1.4 mm (the inset of FIG. 13 shows the offset x=1.4 mm and FIG. 1(c) shows the offset x=0 mm). The gate voltage of a chemFET is proportional to the logarithm of the gas concentration:

$$V_G = m \log_{10} C_{NH3} + n$$

where $V_G$ is the gate voltage in mV, $C_{NH3}$ is the ammonia gas concentration in ppm, m is the sensitivity of the chemFET in mV per logarithmic decade, and n is a constant. This equation can be rewritten in terms of the response in FIG. 13 as follows:

$$(C_b - C_a)/C_a = 10^{(V_{Ga} - V_{Gb})/m} - 1$$

where subscripts a and b denote measurements done "after" and "before" filtering, respectively. The concentrations $C_b$ and $C_a$ were measured at t=5 min and t=10 min, respectively. FIG. 13 shows the 2D responses of the sensor array when (a) x=0 mm and (b) x=1.4 mm. The average of the responses for x=0 mm is $5.0 \times 10^{-3}$ ($\sigma = 1.2 \times 10^{-4}$) and for x=1.4 mm is $4.7 \times 10^{-3}$ ($\sigma = 1.5 \times 10^{-4}$), respectively (where $\sigma$ is the standard deviation). It can be seen from FIG. 13 that there was a slight decrease in the response of the top row of chemFETs (Modules 5 to 8) with respect to the bottom row of chemFETs (Modules 1 to 4) when x=1.4 mm, because the top row was further from the orifice. A horizontal offset of the jet orifice with respect to the array affects the magnitude of the response. This was not surprising because a certain amount of mixing and carry-over of the gas in the cell takes place in the pulsed regime of operation. However, as long as the geometrical configuration remains constant, the quality of the differential mode of measurement was not affected. The patterns of expected (A) and observed (B) experimental performances of the "smart filter" in this example of the present invention are illustrated in FIG. 14, where ammonia was used as the test gas. The direction of one representative sensor response corresponds to that shown in FIG. 11. Panels A-a and B-a show the situation when the incoming flow did not contain detectable gas, which was to be removed by the filter and detected by the sensor. Therefore, the difference of the signals is zero (B-a).

Panels A-b and B-b show that the incoming gas contains ammonia, which is removed by the filter. When the filter breakthrough occurs (panels A-c and B-c) the "zero gas" line is affected, as shown. The pattern shown in panels A-d and B-d indicated simultaneous breakthrough and decrease of ammonia concentration in the incoming air. In principle, it may also correspond to the concurrent loss of sensitivity and breakthrough of the filter. However, these two events are more likely to occur on different time scales.

Example 3

Figure 15:
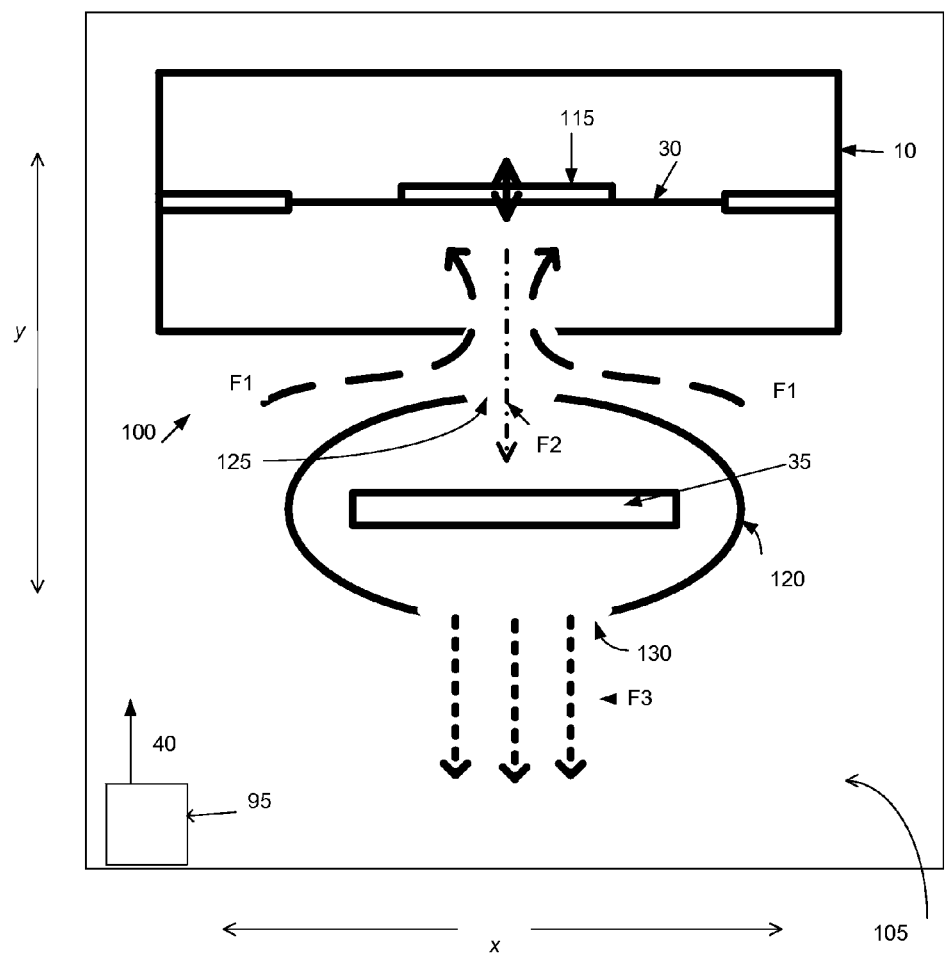
FIG. 15 is a schematic drawing of an alternate embodiment of the present invention in which a fluidic sensing system with an integral jet actuator according to the present invention is employed to monitor a gas present within an ambient environment.

FIG. 15 illustrates yet another exemplary embodiment of the present invention in which a fluidic sampling system incorporating a jet actuator according to the present invention is employed to monitor a gas or liquid present within an ambient environment, but not flowing within a conduit. In FIG. 15, an exemplary gas source 95 is releasing a sample gas 40 into a three-dimensional environment 105 defined by dimensions x, y, and z. FIG. 15 is a two-dimensional drawing, and dimension z is not shown in FIG. 15. As shown in FIG. 15, a fluidic sensing system with an integral jet actuator 100 according to the present invention comprises a jet activator 10 with a jet actuator orifice 25 that serves as both an inlet and outlet for said jet actuator 10 and a sensor 35, enclosed by a sensor enclosure 120 with a sensor inlet 125 (oriented towards the jet actuator orifice 25) and an exhaust outlet 130. In the embodiment shown in FIG. 15, an amount of ambient gas is drawn into the jet actuator 10 as entrained fluid through orifice 25, forming a jet of entrained ambient gas flow F1. Within the jet actuator 10 mechanical action of the movement of a diaphragm 30 controlled by a piezoelectric element 115 delivers a sample gas jet flow F2 which is directed through the orifice 25 into the sensor inlet 125. In various embodiments of the present invention, other control devices including but not limited to electromagnetic or electrostatic control devices may be employed to controllably operate the diaphragm 30. The sample gas jet flow F2 then impacts the sensor 35, and is finally vented through the exhaust outlet 130 into the ambient environment 105 in exhaust flow F3. Orientation of the exhaust flow F3 through the exhaust outlet 130 is maintained to prevent direct recirculation of said exhaust flow F3 into the entrained ambient gas flow F1. The sensor 35 is capable of providing a qualitative and/or quantitative analysis of the gas content of the sample gas jet flow F2, and then transmits data regarding the analysis to a data collection system (not shown in FIG. 15).

In various embodiments of the present invention, the shape or dimensions of the sensor enclosure 120 may vary. Furthermore, embodiments of the present invention may have the relationship between the jet actuator orifice 25 and the sensor inlet 125 as shown in FIG. 15, or there may be a conduit element (not shown in FIG. 15) to direct sample gas jet flow F2 from the jet actuator 10 into the sensor inlet 125. It should further be noted that the orientation of the jet actuator 10 and the sample gas jet flow F2 relative to the sensor 35 may be varied in various embodiments of the present invention, such that the orientation of the jet actuator 10 and the sample gas jet flow F2 may or may not be normal to the sensor 35, as long as the sample gas jet flow F2 impinges on said sensor 35. Such embodiments of the present invention do not require that samples gases or liquids be actively flowing, but can be used to test for targeted gases or liquids in ambient environments. Such ambient environments may be contained with defined dimensions as shown in FIG. 15, or may be uncontained and without defined dimensions.

The embodiments of the present invention are not limited to the particular exemplary embodiments, process steps, and materials disclosed herein as such embodiments, process steps, and materials may vary somewhat. Moreover, the terminology employed herein is used for the purpose of describing exemplary embodiments only and the terminology is not intended to be limiting since the scope of the various embodiments of the present invention will be limited only by the appended claims and equivalents thereof. Thus, while the various embodiments of this invention have been described in detail with particular reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

We claim:

1. A fluidic sampling system comprising one or more fluidic sensors comprising sensing elements and at least one surface thereon, each fluidic sensor in fluid communication with one or more integral active fluidic jet actuators and with a conduit containing one or more sample fluids, wherein said system has a controllable "sniffing" functionality to allow periodic sampling of one or more sample fluids.

2. The fluidic sampling system of claim 1, wherein said active fluidic jet actuators are configured to deliver one or more sample gases to said fluidic sensors.

3. The fluidic sampling system of claim 1, wherein said active fluidic jet actuators are configured to create spatially controlled jet fields to induce small-scale fluid motion near the surface of said fluidic sensors to overcome diffusion-limited mass transfer at the surface of the sensing elements.

4. The fluidic sampling system of claim 1, wherein said active fluidic jet actuators are further provided to controllably create a spatially controlled jet field to deliver a flushing gas to clean or calibrate said fluidic sensors.

5. The fluidic sampling system of claim 1, wherein said system further comprises at least one filter within a flow path of said one or more sample fluids.

6. The fluidic sampling system of claim 5, wherein said system is further provided to allow sampling of said one or more sample fluids upstream of and downstream of said filter, thereby allowing monitoring and assessment of filter function.

7. The fluidic sampling system of claim 1, wherein said one or more sample fluids comprise one or more gases or gas mixtures.

8. The fluidic sampling system of claim 1, wherein said one or more sample fluids comprise one or more liquids or liquid mixtures.

9. The fluidic sampling system of claim 1, wherein said one or more sample fluids are flowing within a contained space or conduit.

10. The fluidic sampling system of claim 1, wherein said one or more sample fluids are static within an environment.

11. The fluidic sampling system of claim 1, wherein said one or more sample fluids are contained within an enclosure.

12. The fluidic sampling system of claim 1, wherein said system comprises two or more fluidic sensors comprising sensing elements and at least one surface thereon, each fluidic sensor in fluid communication with one or more integral active fluidic jet actuators and with a conduit containing one or more sample fluids, wherein said two or more fluidic sensors provide a redundant monitoring and assay function to ensure against aberrant sensor function.

13. The fluidic sampling system of claim 1, wherein the conduit comprises a first end in fluid communication with an ambient environment for receiving the one or more sample fluids.

14. The fluidic sampling system of claim 1, wherein the one or more integral active fluidic jet actuators is configured to cause the one or more sample fluids to impinge normal to the one or more fluidic sensors.

15. The fluidic sampling system of claim 1, wherein each of the one or more active fluidic jet actuators comprises a diaphragm configured to oscillate at a predetermined frequency.

16. The fluidic sampling system of claim 15, wherein the predetermined frequency is between about 100 Hz and about 2000 Hz.

17. The fluidic sampling system of claim 15, wherein the predetermined frequency is substantially a fundamental frequency of the diaphragm.

18. The fluidic sampling system of claim 15, wherein the predetermined frequency is substantially a harmonic of a fundamental frequency of the diaphragm.

19. A method of sensing one or more fluids within a conduit, wherein said conduit is in fluid communication with one or more fluidic sensors oriented in position with one or more active fluidic jet actuators, the method comprising:
    oscillating a diaphragm of said one or more jet actuators to create a spatially controlled jet field to deliver one or more sample fluids to said fluidic sensors and to induce small-scale fluid motion near the surface of said fluidic sensors; and
    periodically sampling the one or more sample fluids.

20. The method of claim 19, wherein the delivery of said sample fluids to said fluidic sensors imparts substantially no effect on concentration or other chemical qualities of said one or more sample fluids within said conduit.

21. The method of claim 19, wherein said one or more sample fluids are static within said conduit.

22. The method of claim 19, wherein said one or more sample fluids are flowing within said conduit.

23. The method of claim 22, wherein the delivery of said sample fluids to said fluidic sensors imparts substantially no effect on the flow of said one or more sample fluids are flowing within said conduit.

24. The method of claim 19, wherein each of the one or more fluidic active fluidic jet actuators comprises a diaphragm, the method further comprising oscillating the diaphragm at a predetermined frequency.

25. The method of claim 24, wherein the predetermine frequency is one of a fundamental frequency of the diaphragm and a harmonic of the fundamental frequency of the diaphragm.

26. A method of sensing one or more fluids within an environment with a fluidic sampling system comprising one or more fluidic sensors, wherein each fluidic sensor is in fluid communication with one or more integral fluidic jet actuators, wherein said environment is in fluid communication with said one or more fluidic sensors, the method comprising:
    creating a spatially controlled jet field with said jet actuators to deliver one or more sample fluids to said fluidic sensors and to induce small-scale fluid motion near the surface of said fluidic sensors; and
    controllably "sniffing" with said system to periodically sample said one or more sample fluids.

27. The method of claim 26, wherein the delivery of said sample fluids to said fluidic sensors imparts substantially no effect on concentration or other chemical qualities of said one or more sample fluids within said environment.

28. The method of claim 26, wherein said one or more sample fluids are static within said environment.

29. The method of claim 26, wherein said one or more sample fluids are flowing within said environment.

30. The method of claim 29, wherein the delivery of said sample fluids to said fluidic sensors imparts substantially no effect on the flow of said one or more sample fluids flowing within said environment.

* * * * *